United States Patent
Flanagan

(10) Patent No.: US 6,554,854 B1
(45) Date of Patent: Apr. 29, 2003

(54) PROCESS FOR LASER JOINING DISSIMILAR METALS AND ENDOLUMINAL STENT WITH RADIOPAQUE MARKER PRODUCED THEREBY

(75) Inventor: Aiden Flanagan, Galway (IE)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/458,851

(22) Filed: Dec. 10, 1999

(51) Int. Cl.[7] .................................................. A61F 2/06
(52) U.S. Cl. ....................................................... 623/1.1
(58) Field of Search .............................. 623/1.46, 1.15, 623/1.34, 1.44; 606/194, 195, 198; 148/22; 219/121.63, 121.64

(56) References Cited

U.S. PATENT DOCUMENTS

| | | | |
|---|---|---|---|
| 4,348,263 A | 9/1982 | Draper et al. | 204/29 |
| 4,495,255 A | 1/1985 | Draper et al. | 428/669 |
| 5,274,210 A | * 12/1993 | Freedman et al. | 219/121 |
| 5,964,963 A | * 10/1999 | Turchan et al. | 148/22 |
| 6,174,329 B1 | * 1/2001 | Callol et al. | 623/1.34 |
| 2001/0001317 A1 | * 5/2001 | Duerig et al. | 623/1.15 |

FOREIGN PATENT DOCUMENTS

| | | |
|---|---|---|
| EP | 0 491 959 | 7/1992 |
| EP | 0 824 900 | 2/1998 |
| WO | 98/46168 | 10/1998 |
| WO | 00/64375 | 11/2000 |

OTHER PUBLICATIONS

S. Schiller et al., "Electron Beam Surface Hardening," ASM Handbook, Vol. 4—Heat Treating, 1991.
J.F. Ready, "Laser Applications," vol. 5, Academic Press, 1984, pp. 82–91.

* cited by examiner

Primary Examiner—Michael J. Milano
Assistant Examiner—Vy Q. Bui
(74) Attorney, Agent, or Firm—RatnerPrestia

(57) ABSTRACT

A process for laser joining a first metal, having a first reflectance curve as a function of wavelength, such as nitinol or stainless steel, and a second metal, having a second reflectance curve, such as gold. The process comprises placing the first and second metals in contact with one another then exposing at least one of the first metal and second metal to a laser beam having a wavelength selected from an optimal range of wavelengths over which the reflectance curves of the two metals essentially overlap. The first metal may comprise a first metal element having a sufficiently low heat sink capacity and a sufficiently lesser reflectance than the second metal at wavelengths outside the optimal range of wavelengths such that laser joining at such wavelengths exposes the first metal to a risk of excessive melting, vaporization, or cutting through the first metal element. The first metal element may be a stent adapted for endoluminal deployment, wherein the second metal is a radiopaque marker relative to the first metal. A stent produced by this process may comprise one or more first metal elements with a radiopaque marker metal attached to one or more portions of at least one element, the radiopaque marker comprising the second metal attached to the first metal by a weld, a clad layer of the second metal over the first metal, or an alloy layer of the two metals over the first metal.

21 Claims, 4 Drawing Sheets

PROCESS FOR LASER JOINING DISSIMILAR METALS AND ENDOLUMINAL STENT WITH RADIOPAQUE MARKER PRODUCED THEREBY

TECHNICAL FIELD

This invention relates generally to joining dissimilar metals by use of a laser and, more specifically, to laser joining gold onto wires of an endoluminal stent.

BACKGROUND OF THE INVENTION

A stent is an elongated device used to support an intraluminal wall. In the case of a stenosis, a stent provides an unobstructed conduit for blood in the area of the stenosis. Such a stent may also have a prosthetic graft layer of fabric or covering lining the inside or outside thereof, such a covered stent being commonly referred to in the art as an intraluminal prosthesis, an endoluminal or endovascular graft (EVG), or a stent-graft.

A prosthesis may be used, for example, to treat a vascular aneurysm by removing the pressure on a weakened part of an artery so as to reduce the risk of rupture. Typically, a prosthesis is implanted in a blood vessel at the site of a stenosis or aneurysm endoluminally, i.e. by so-called "minimally invasive techniques" in which the prosthesis, restrained in a radially compressed configuration by a sheath or catheter, is delivered by a deployment system or "introducer" to the site where it is required. The introducer may enter the body through the patient's skin, or by a "cut down" technique in which the entry blood vessel is exposed by minor surgical means. When the introducer has been threaded into the body lumen to the prosthesis deployment location, the introducer is manipulated to cause the prosthesis to be ejected from the surrounding sheath or catheter in which it is restrained (or alternatively the surrounding sheath or catheter is retracted from the prosthesis), whereupon the prosthesis expands-to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Various types of stent architectures are known in the art, including many designs comprising a filament or number of filaments, such as a wire or wires, wound or braided into a particular configuration. Other non-wire stent architectures may comprise a tubular sleeve of metal that is laser cut into an expandable and collapsible design. Often, during implantation of wire stents into a body lumen, the attending surgeon or other member of the surgical team needs to view the positioning of the stent within the lumen using fluoroscopy. Thus, radiopaque markers are often used, a radiopaque marker being any portion of a stent that has a different fluoroscopic reflectance than surrounding portions of the stent. As most stent wires comprise nitinol (a nickel-titanium alloy) or stainless steel, one metal that can serve as such a fluoroscopic marker is gold.

It is known in the art to attach gold to the other metal by electro-plating, by physical attachment such as winding a marker band around a portion of the wire or sliding a gold hypotube over the wire like a sleeve, by ion implantation methods, or by welding methods such as arc-welding. It is also known to weld gold with an electron beam. Electroplating generally provides only a thin coat of gold having an undesirably rough surface, and generally results in poor adhesion of the gold to nitinol. Ion implantation methods generally may also have poor adhesion to some metals such as nitinol. Arc-welding methods, although applicable for joining gold to other metals on a large scale, are inapplicable for the small scale of stent construction. Physical attachment is labor intensive and generally is inapplicable to non-wire stents such as laser-cut tubular stents. Physical attachment to wire stents typically comprises threading a marker band hypotube onto the stent wire before or during winding the stent on a mandrel. Electron beam welding equipment is capital intensive and is less flexible that laser beam welding, as electron beam welding requires performing the welding process in a vacuum.

Laser welding of gold to stent wires using a commercially available Nd:YAG (neodymium:yttrium-aluminum-garnet) laser at a standard wavelength of 1.064 µm has been tried with variable success. One problem with performing such laser welding processes is the difficulty in selecting an optimum laser intensity, because the temperature rise in gold is typically much lower than the temperature rise in the metal to which the gold is being welded. Thus, a laser intensity that heats the gold to the proper temperature may heat the surrounding stent wire metal to a temperature that is so high that it causes excessive melting, vaporization, and/or cutting of the small-diameter stent wire to which the gold is to be welded. Similarly, if the wire is inadequately covered by the gold, leaving portions of the wire exposed during the welding step, or if the gold to be welded has a variable thickness, even if the precise intensity for welding one section is selected, that intensity may cause the same melting, vaporization, and/or cutting problems where the wire is exposed or the gold is thinner.

Thus, there is a need in the art to provide a reliable process for joining gold to other metals, specifically for laser processing of gold onto metal stent wires.

SUMMARY OF THE INVENTION

In view of the shortcomings of the prior art, the present invention provides a process for joining a first metal, having a first reflectance curve as a function of wavelength, with a second metal, having a second reflectance curve, through the use of a laser. The process comprises placing the first metal in contact with the second metal and exposing at least one of the first metal and second metal to a laser beam having a wavelength selected from an optimal range of wavelengths over which the first reflectance curve and the second reflectance curve essentially overlap. The first metal may be nickel, titanium, iron, or an alloy thereof, and the second metal may be gold or copper. With the wavelengths of the laser beam selected to be over an optimum range, any adverse effect caused by one of the metals heating significantly due to a difference in reflectance is avoided. The laser joining can involve bonding the two metals in some way, such as by welding, cladding, or alloying.

The invention also includes a stent adapted for endoluminal deployment within a body lumen made by the process described above. Such a stent includes one or more first metal elements each comprising a first metal and a radiopaque marker metal attached to one or more portions of at least one element. The radiopaque marker comprises a second metal attached to the first metal by one of: a weld, a clad layer of the second metal over the first metal, an alloy layer of the first metal and the second metal over the first metal, or a combination thereof. The attachment process uses a laser having a wavelength within the optimal range, as described above.

It is to be understood that both the foregoing general description and the following detailed description are exemplary, but are not restrictive, of the invention.

DETAILED DESCRIPTION OF INVENTION

The invention will next be illustrated with reference to the figures wherein similar numbers indicate the same elements in all figures. Such figures are intended to be illustrative rather than limiting and are included herewith to facilitate the explanation of the apparatus of the present invention.

Figure 1:
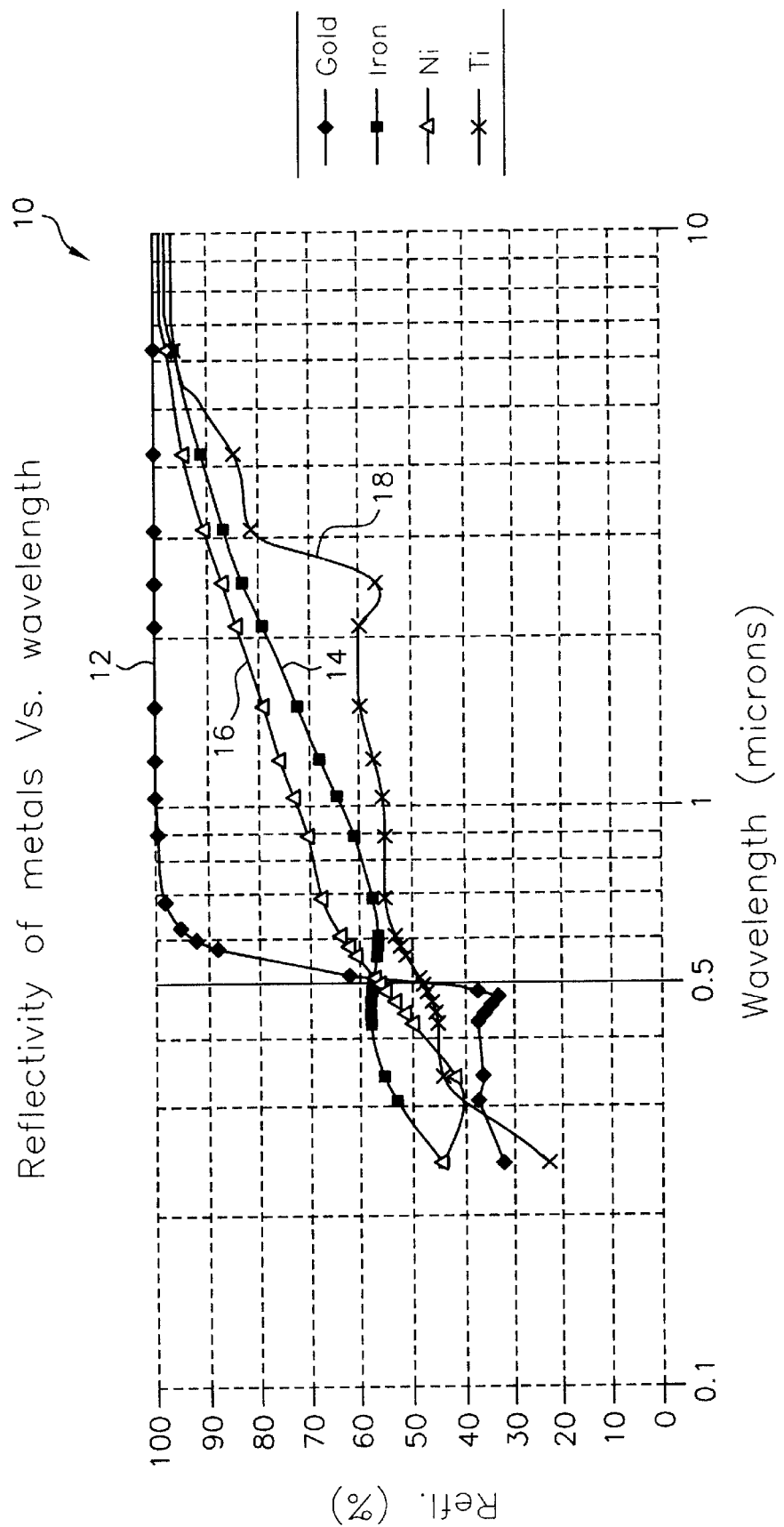
FIG. 1 is a graph illustrating the percent reflectance of incident light for different metals as a function of the wavelength in microns of the incident light.

Referring now to FIG. 1, there is shown a semi-logarithmic graph 10 of percent reflectance for various metals versus the wavelength in microns of the incident light on the metal. Reflectance is a measure of the amount of energy reflected from a surface (as opposed to absorbed by the surface) as a percentage of the energy incident on the surface. FIG. 1 shows curves for gold 12, iron 14, nickel (Ni) 16, and titanium (Ti) 18. Curve 14 for iron is representative of a similar curve for stainless steel. Curves 16 and 18 for nickel and titanium, respectively, are similarly representative of the curve for nitinol (a nickel-titanium alloy), which is an interpolation of the two curves, depending upon the percentage of each metal in the alloy.

As can be seen from the graph, reflectance curve 12 for gold differs greatly from reflectance curves 14, 16, and 18 for iron, nickel, and titanium, respectively. This difference explains the mismatch between the metal temperature of gold as compared to that of nitinol or stainless steel for laser processing at the 1.064 µm wavelength. In particular, in the range of wavelengths between approximately 0.6 µm and 3 µm, the higher reflectance of gold as compared to the other metals means that the other metals absorb more laser energy (thus heating the metal more) whereas the gold reflects much of the energy (thus remaining relatively less heated). Thus, by utilizing a wavelength in the range of wavelengths where the reflectance curves approach each other or essentially overlap, metals having different reflectance curves may be joined by a laser welding process without some of the problems experienced in the ranges where the reflectances are mismatched. The necessary degree of similarity between the reflectance curves is a function of other process parameters, such as the intensity of the light, the materials being used, and the thickness of the materials. It is preferable, however, that the optimal range of wavelengths includes only those wavelengths where the reflectance percentages of the metals being processed differs by no more than 15% (on an absolute scale), more preferably no more than 10%, and still more preferably no more than 5%. Ideally, the percent reflectance differs by no more than 2%. As used herein, the term "essentially overlaps" shall refer to a range of wavelengths over which there is no significant melting, vaporization, or cutting of one of the metals due to heating of that metal caused by a difference in reflectance. As mentioned above, the particular difference where this occurs depends on other process parameters, but in general, at reflectance difference percentages of 15% or less no significant melting, vaporization, or cutting is likely to occur.

Figure 2A:
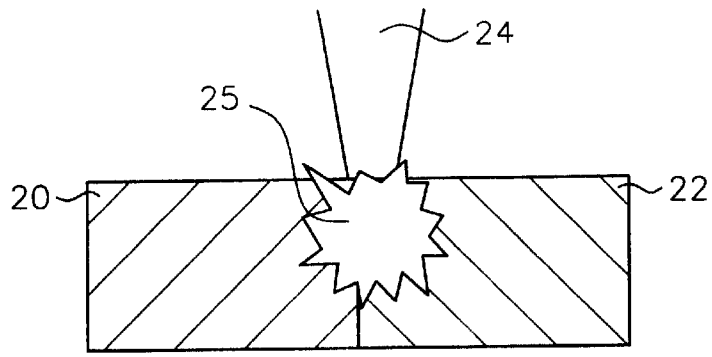
FIG. 2A is a cross sectional illustration of a first metal and second metal being joined in accordance with the present invention.
Figure 2B:
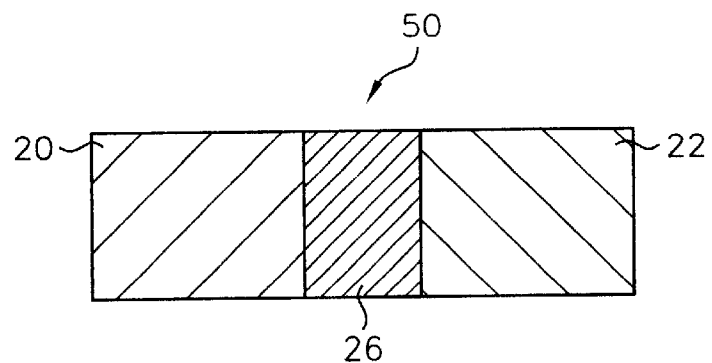
FIG. 2B is a cross sectional illustration of a first metal and second metal after being joined in accordance with the present invention.
Figure 3:
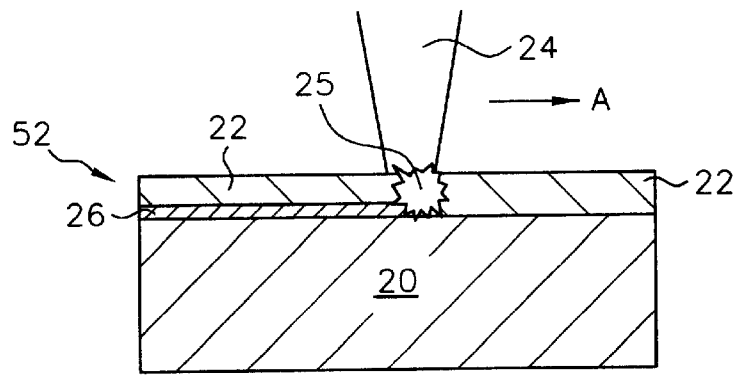
FIG. 3 is a longitudinal sectional illustration of a second metal being clad over a first metal in accordance with the present invention.

Referring now to FIGS. 2A–4, the invention comprises a process for laser joining a first metal 20, such as nitinol or stainless steel, having a first reflectance curve as a function of wavelength, such as a curve similar to curves 14, 16, or 18, and a second metal 22, such as gold having a second reflectance curve 12. The phrase "laser joining" includes, for example, welding (such as is illustrated in FIGS. 2A and 2B), cladding (such as is illustrated in FIG. 3), or alloying (such as is illustrated in FIG. 4A) of two or more dissimilar metals by using a laser 24. All of these laser joining processes essentially comprise laser heating of an area where two different metals interface, thus causing the metals to melt together to create an alloy of the two metals.

Figure 4:
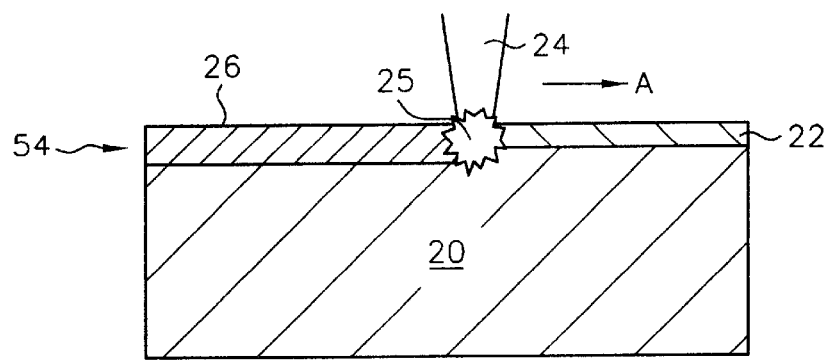
FIG. 4 is a longitudinal sectional illustration of a second metal forming an alloy with a first metal in an alloy layer over the first metal.

As shown in FIG. 2A, laser welding typically comprises joining two abutting metal surfaces 20 and 22 together as a result of the dissipation of energy 25 from laser beam 24 melting both metals. The melted metals then mix together in the form of an alloy 26 as shown in FIG. 2B. Weld 50 can be a continuous weld over an extensive length or a spot weld confined to a relatively small area. Laser cladding, as shown in FIG. 3, typically comprises adhering metal 22 as a surface layer to metal 20 as laser 24 moves in the direction of arrow A, where alloy layer 26 results as an intermediate layer between the two metals, but a discrete layer of metal 22 still remains on the surface. Laser alloying, on the other hand, as shown in FIG. 4, typically comprises forming an alloy layer 26 comprising metal 22 and metal 20, where the alloy layer completely replaces layer 22 on the surface of metal 20 as laser 24 moves in the direction of arrow A.

The process according to the present invention comprises processing first metal 20 and second metal 22 using a laser beam 24 having a wavelength selected from an optimal range of wavelengths over which the first reflectance curve and the second reflectance curve (as shown in FIG. 1) essentially overlap. The laser joining may comprise welding second metal 22 to the first metal 20, cladding the first metal with the second metal, laser alloying the first and second metals, or a combination thereof. Other than selecting the wavelength to be in an optimal range as described herein, all other laser processing conditions can readily be determined by one skilled in the art as the application requires.

Although this process is particularly advantageous for laser joining a second metal 22 that is a radiopaque marker made of gold to a first metal 20 that is an element of a stent made of nitinol or stainless steel, the process is equally applicable for use in other applications with other metals. In particular, the process may be used for laser joining other metals having reflectance curves similar to gold, such as copper, with other metals such as nickel, titanium, or iron, or alloys of those metals, or any metals having curves similar to the curves shown in FIG. 1. More generally, the process may be used with any two metals whose reflectance curves essentially overlap over some optimal range of wavelengths. In general, yellowish metals such as gold, copper, and brass tend to have different reflectance curves than silvery metals such as steel, nickel, or titanium. This generalization based on metal color is not an exclusive determination of which metals may have different curves, however, as other metals may have different reflectance curves in the area of interest (such as the 0.2516 $\mu$m–1.064 $\mu$m range over which a Nd:YAG laser typically operates) without necessarily having a difference in the visible wavelengths (0.39–0.77 $\mu$m).

The process of this invention is applicable to the laser joining of any two or more metals that have respective reflectance curves having overlapping portions as well as significantly disparate portions within the wavelengths at which the laser operates. The process is particularly useful in applications where the heat sink capacity of the first metal element 20 is relatively low due to its relative thickness, such as for example in a stent wire or in electronics or jewelry applications where there is a risk of a relatively low-mass element being excessively melted, cut, or vaporized because of the disparity between reflectance curves outside of the optimal range of wavelengths. A skilled technician in the art can recognize applications having such risks given the mass of the elements to be welded, the intensity of the laser, and the absorbency of laser energy at the wavelengths to be applied.

For example, a simple estimate of temperature rise at the surface of a material (ignoring latent heat effects) can be calculated. The basic heat conduction equation given by Fourier's law in terms of the rate of heat transfer q across an area A in a solid is:

$$q = -KA\frac{\delta T}{\delta x} \quad (1)$$

where $$\frac{\delta T}{\delta x}$$

is the temperature gradient in the direction normal to A and K is the thermal conductivity of the solid. From equation 1, the heat conduction equation can be derived as:

$$\nabla^2 T + \frac{Q(x, y, z, t)}{K} = \frac{1}{\kappa}\frac{\delta T}{\delta t} \quad (2)$$

where $\kappa = K/\rho c$ is the thermal diffusivity, Q(x,y,z,t) is the rate of internal heat generation per unit volume, and $$\frac{\delta T}{\delta t}$$

is the rate of change of temperature. Solving the equation for the simplified case of an infinite half space with a uniform surface heat flux created by the incident laser beam, the temperature at the surface at any time t can be calculated as follows:

$$T(t) = \frac{2\varepsilon I}{K}\left(\frac{\kappa t}{\pi}\right)^{1/2} \quad (3)$$

where I is the laser intensity and $\epsilon$ is the emissivity of the material surface. The emissivity is related to the reflectivity R by $\epsilon=(1-R)$.

Figure 5:
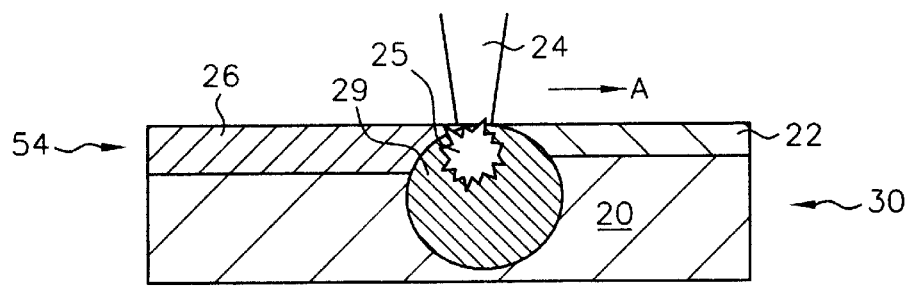
FIG. 5 is a longitudinal sectional illustration of a second metal forming an alloy with a first metal in an alloy layer over the first metal in accordance with the prior art wherein the laser wavelength coincides with a mismatched reflectivity of the first and second metals.

FIG. 5 illustrates how selection of a wavelength outside the optimal range may result in a region 29 of excessive melting within an element 30 comprising first metal 20 and having a relatively low heat sink capacity (i.e., low enough thermal mass such that localized overheating can cause element 30 to be cut, vaporized, or excessively melted), such as a wire or cut tubular element of a stent. Although a first laser pulse may produce layer 54 of alloy 26 of first metal 20 and second metal 22, an overlapping laser pulse may subsequently hit the alloy layer. Because alloy 26 has a much lower reflectance than second metal 22, the alloy absorbs more energy than desired, and an excessively melted region 29 forms, creating a different alloy than alloy 26 and potentially nearly cutting through element 30.

As shown in FIG. 1, the optimal range of wavelengths for gold and iron, nickel, or titanium where curve 12 approaches (essentially overlaps) curves 14, 16, and 18, is at wavelengths less than approximately 0.55 $\mu$m or greater than approximately 3 $\mu$m. Because the reflectance is high above 3 $\mu$m, however, use of wavelengths above 3 $\mu$m tends to be more inefficient, as very little of the energy is actually absorbed by the metals as compared to what is emitted by the laser. At wavelengths below 0.4 $\mu$m, the wavelength approaches the ultraviolet band, which is less efficient for heating metal. Thus, a preferred range of wavelengths for gold and stainless steel or nitinol comprises wavelengths between approximately 0.40 $\mu$m and approximately 0.55 $\mu$m. A frequency-doubled Nd:YAG laser, which are commercially available, provides a wavelength of 0.532 $\mu$m, and is therefore ideal for providing the processing wavelengths. Other Nd lasers (not YAG based), such as a Nd:YLF laser at doubled frequency, or a metal vapor laser, may also provide a wavelength in this range. Although a $CO_2$ laser can be used for welding gold to other metals because of the capability of providing energy in the 10 $\mu$m range where the reflectance curves have only very small differences among them, $CO_2$ lasers typically do not have the same short pulse characteristics as YAG lasers. Short pulses are desirable for welding items having low mass, such as stent materials.

Figure 6:
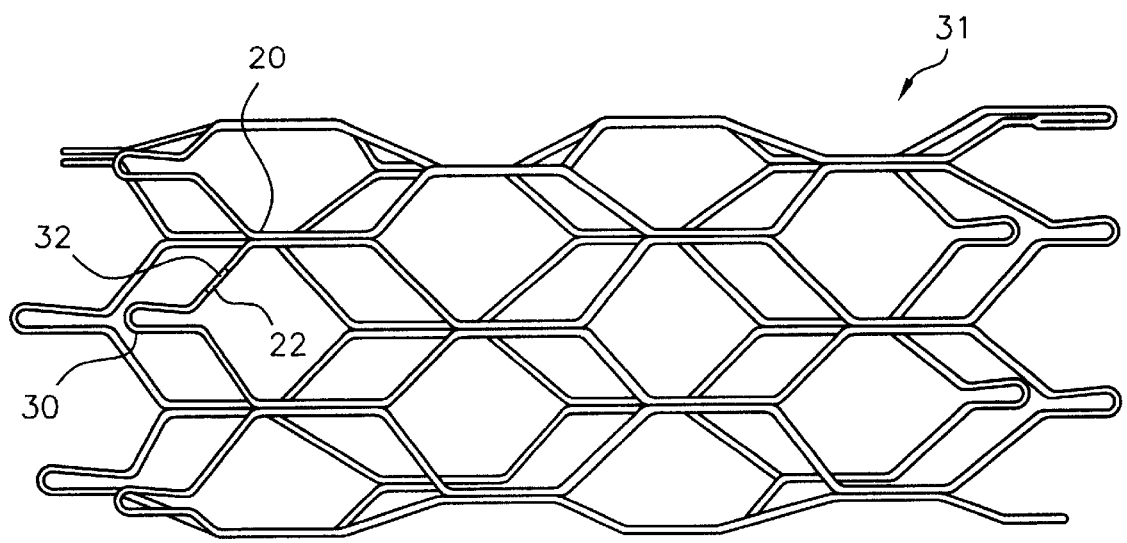
FIG. 6 is a side plan view of a stent in accordance with the present invention, showing a radiopaque marker.
Figure 7:
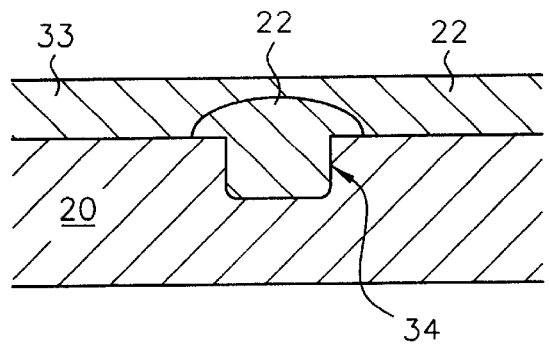
FIG. 7 is a longitudinal sectional illustration of an element of a stent having a pithole in the stent element filled with a radiopaque marker metal.

In particular, referring now to FIGS. 6–10, first metal 20 may be an element 30 of a stent, such as exemplary stent 31 shown in FIG. 6, adapted for endoluminal deployment. Second metal 22 may form a radiopaque marker 32 having a greater or lesser fluoroscopic reflectance than first metal 20, such as gold over stainless steel or nitinol. As shown in FIG. 7, the process may further comprise forming pitholes 34 in the first metal stent element 30 and then filling the pitholes with the second metal 22. An additional layer 33 of second metal 22 may optionally be added over the first metal stent element 30 and pitholes 30 filled with the second metal.

Figure 8:
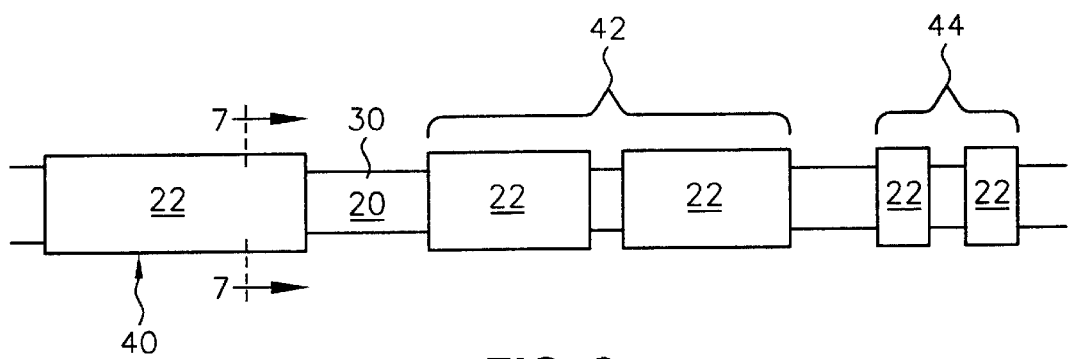
FIG. 8 is a sideplan view of an element of a stent, showing various radiopaque marker patterns according to the present invention.
Figure 9:
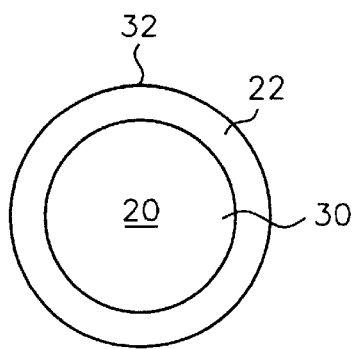
FIG. 9 is a cross-sectional view of an element of a wire stent having a radiopaque marker cladding over the entire periphery of the wire element.
Figure 10:
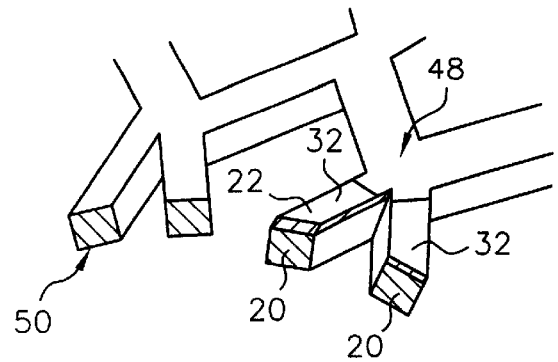
FIG. 10 is a perspective, partial cross-sectional view of a laser-cut tubular element of a stent having a radiopaque marker cladding over only the outwardly facing side of the element.

As shown in FIG. 8, the process may further comprise attaching second metal 22 to stent element 30 to create radiopaque marker 32 having a pattern comprising an unbroken line 40 along the stent element, a broken line 42 along the stent element, a dot pattern 44 along the stent element, or some combination thereof as shown in FIG. 8. The pattern of lines or dashes may be arranged to provide a guide in the form of a ruler, if desired. As shown in cross-section in FIG. 9, radiopaque marker 32 may comprise second metal 22 attached to stent element 30 over the entire peripheral surface 46 of the stent element, or, as shown in FIG. 10, only over a portion 48 of the peripheral surface. In particular, radiopaque marker 32 may comprise second metal 22 attached to stent element 30 only over outwardly facing surface 48, leaving inwardly facing surface 50 uncovered. Stent element 30 may be a wire element such as is shown in FIG. 9, a laser cut tubular element, such as is shown in FIG. 10, or any type of metal element known in the art.

To join the two metals, for example, a gold wire may be placed adjacent the stainless steel or nitinol wire or element, and the laser focused on the wire. The pulses of the laser then fuse the wires together. Where the gold wire is small relative to the other metal wire, the gold may adhere to the other wire only on the top surface where the wire was placed. Other size gold wires may melt and completely envelop the nitinol or stainless steel element.

The stents created by the laser welding process described herein are marked by good adherence of the gold to the underlying metal in the form of a welded, clad, or laser alloyed area. Such a welded, clad, or alloyed area produced by laser joining differs from corresponding structures produced by electron welding. This difference is a result of the energy absorption process. The absorption of laser radiation essentially occurs in the first few hundred nanometers of the metal surface. The electron beam is absorbed in a relatively thick layer S ($\mu$m) that is given by:

$$S = (2.1 \times 10^{-8}) \frac{U_B^2}{\rho} \quad (4)$$

where $U_B$ is the acceleration voltage of the electron beam in volts and $\rho$ is the density of the material in g/cm$^3$. For most metals this equates to an absorption layer of approximately 10 to 50 $\mu$m. Metal under the absorption layer is heated by conduction. Therefore, the entire absorption layer reaches the melting point for a process requiring melting. For a stent strut that is typically only 100 $\mu$m deep, the absorption layer represents a significant portion of the overall depth. In a laser process where the laser energy is incident on the surface of the metal and the amount of energy can be controlled via the laser intensity, however, the melting depth can be chosen more accurately than by electron beam welding. Thus, structures welded, clad, or alloyed by an electron beam process may typically comprise larger molten and heat-affected zones than a laser process, particularly in small structures such as stents or small-diameter wires.

As shown in FIG. 6, the invention also comprises a stent 31 adapted for endoluminal deployment within a body lumen (not shown). The stent comprises one or more first metal elements 30, each comprising first metal 20, and a radiopaque marker 32 comprising a second metal 22 attached to one or more portions of at least one element. Second metal 22 may be laser joined to first metal 20 by a weld 50 as shown in FIG. 2B, as a clad layer 52 of the second metal over the first metal as shown in FIG. 3, as an alloy layer 54 as shown in FIG. 4, or in a combination thereof.

The resulting laser-processed gold (or other metal) portions of the stent (or other object), by virtue of the strong bond provided by the alloy (whether as an alloy layer 54 as shown in FIG. 4, a weld 50 as shown in FIG. 2B, or as a layer between clad layer 52 and the supporting metal 20 as shown in FIG. 3), is capable of being polished. The connection also prevents movement of the marker band along the stent wire, unlike known movement that occurs with pre-existing hypotube marker bands threaded on stent wires. The process of this invention allows the use of laser joining, which is less labor-intensive than physical attachment processes, and allows the attachment of the marker bands on the finished stent, rather than requiring threading the hypotube onto the wire during fabrication. The gold can be alloyed or clad onto the other metal in a thin surface layer that does not affect bulk mechanical properties.

EXAMPLE

The following example is included to more clearly demonstrate the overall nature of the invention. This example is exemplary, not restrictive, of the invention.

The following table gives the thermophysical and emissivity values for gold and iron (approximately the same as for stainless steel):

TABLE 1

|  | GOLD | IRON |
| --- | --- | --- |
| Nd: YAG emissivity @ 1064 nm | 0.009 | 0.359 |
| Nd: YAG emissivity @ 532 nm | 0.35 | 0.43 |
| K (W/cmK) | 3.18 | 0.84 |
| κ (cm$^2$/s) | 1.22 | 0.28 |
| Melting point (° C.) | 1064 | 1535 |
| Boiling point (° C.) | 3080 | 2750 |

Using formula 3 recited herein and the laser parameters below, the following estimated temperature rise at a time of 0.1 second results:

TABLE 2

| LASER PARAMETERS | GOLD | IRON |
| --- | --- | --- |
| 1064 nm<br>I 32 1.0 × 10$^5$ W/cm$^2$ | 112° C. | 8070° C. |
| 532 nm<br>I = 3.0 × 10$^4$ W/cm$^2$ | 1300° C. | 2900° C. |

As shown above, the temperature rise for iron is more than 70 times greater than for gold at the 1064 nm wavelength. Thus, significant problems due to overheating of the iron may occur when laser processing gold and iron at this wavelength. At the 532 nm laser wavelength, however, the difference in temperature rise between the two metals is reduced greatly, as iron experiences little more than twice the temperature rise as gold. Therefore, laser processing of the two materials is greatly facilitated at the 532 nm wavelength in accordance with this invention.

While the present invention has been described with respect to specific embodiments thereof, it is not limited thereto. Therefore, the claims that follow are intended to be construed to encompass, not only the specific embodiments described but also all modifications and variants thereof which embody the essential teaching thereof.

What is claimed:

1. A process for laser joining a first metal with a second metal, the first metal comprising an element of a stent adapted for endoluminal deployment and having a first reflectance curve as a function of wavelength, the second metal comprising a radiopaque marker relative to the first metal and having a second reflectance curve, die first metal having a sufficiently lesser reflectance than the second metal outside an optimal range of wavelengths over which the first reflectance curve and the second reflectance curve essentially overlap such that laser processing at a wavelength outside the optimal range exposes the first metal to a risk of excessive melting, vaporization, or cutting through the first metal clement, the process comprising placing the first metal in contact with the second metal and exposing at least one of the first metal and second metal to a laser beam having a wavelength selected from the optimal range of wavelengths, the process comprising first creating pitholes in the first metal stent element and then filling the pitholes with the second metal.

2. The process of claim 1 wherein the step of exposing at least one of the first metal and the second metal to a laser beam comprises welding the second metal to the first metal, cladding the first metal with the second metal, alloying the first metal and the second metal, or a combination thereof.

3. The process of claim 1 wherein the second metal is one of: gold or copper.

4. The process of claim 1 wherein the first metal is one of: nickel, titanium, iron, or an alloy thereof.

5. The process of claim 4 wherein the alloy comprises one of: nitinol or stainless steel.

6. The process of claim 4 wherein the second metal is gold.

7. The process of claim 6 wherein the optimal range of wavelengths consists of: wavelengths less than approximately 0.55 $\mu$m or greater than approximately 3 $\mu$m, wherein the first metal comprises an element of a stent adapted for endoluminal deployment and the second metal comprises a radiopaque marker relative to the first metal.

8. The process of claim 7 wherein the optimal range of wavelengths consists of: wavelengths between approximately 0.40 $\mu$m to approximately 0.55 $\mu$m.

9. The process of claim 8 wherein the selected wavelength is approximately 0.532 $\mu$m.

10. The process of claim 9 wherein the laser beam is generated by a frequency-doubled Nd:YAG laser.

11. The process of claim 1 wherein the first metal comprises an element of a stent adapted for endoluminal deployment and the second metal comprises a radiopaque marker relative to the first metal and the laser beam is generated by a YAG laser.

12. The process of claim 11 wherein the YAG laser is an Nd:YAG laser.

13. The process of claim 1 wherein the first metal comprises one of: nitinol or stainless steel, and the second metal comprises one of: gold or copper.

14. The process of claim 1 further comprising adding an additional layer of the second metal over the first metal stent element and the pitholes filled with the second metal.

15. The process of claim 1 further comprising attaching the radiopaque marker second metal to the stent element first metal in a pattern comprising one of: an unbroken line along the stent element, a broken line along the stent element, a dot pattern along the stent element, or a combination thereof.

16. The process of claim 1 wherein the stent element first metal has a peripheral surface, the process further comprising attaching the radiopaque marker second metal to the stent element first metal over: all of the peripheral surface of the element or a part of the peripheral surface of the element.

17. A stent produced by the process according to claim 1.

18. A stent produced by the process according to claim 13.

19. The process of claim 7, wherein the step of exposing at least one of the first metal and the second metal to a laser beam comprises welding the second metal to the first metal.

20. The process of claim 7, wherein the step of exposing at least one of the first metal and the second metal to a laser beam comprises cladding the first metal with the second metal.

21. The process of claim 1, wherein the step of placing the first metal in contact with the second metal comprises placing a wire of the first metal in contact with a wire of the second metal.

* * * * *

UNITED STATES PATENT AND TRADEMARK OFFICE
CERTIFICATE OF CORRECTION

PATENT NO. : 6,554,854 B1
DATED : April 29, 2003
INVENTOR(S) : Aiden Flanagan

It is certified that error appears in the above-identified patent and that said Letters Patent is hereby corrected as shown below:

<u>Column 9,</u>
Line 1, "die" should be -- the --.
Line 17, "comprises" should be -- comprises: --.

Signed and Sealed this

Twenty-first Day of March, 2006

JON W. DUDAS
*Director of the United States Patent and Trademark Office*